US010967377B2

(12) United States Patent
Kato (10) Patent No.: US 10,967,377 B2
(45) Date of Patent: Apr. 6, 2021

(54) MULTI-WELL PLATE

(71) Applicant: NATIONAL INSTITUTE OF ADVANCED INDUSTRIAL SCIENCE AND TECHNOLOGY, Tokyo (JP)

(72) Inventor: Yoshio Kato, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 225 days.

(21) Appl. No.: 16/314,819

(22) PCT Filed: Nov. 11, 2016

(86) PCT No.: PCT/JP2016/083522
§ 371 (c)(1),
(2) Date: Jan. 2, 2019

(87) PCT Pub. No.: WO2018/012002
PCT Pub. Date: Jan. 18, 2018

(65) Prior Publication Data
US 2019/0329243 A1 Oct. 31, 2019

(30) Foreign Application Priority Data
Jul. 15, 2016 (JP) .............................. JP2016-140573

(51) Int. Cl.
*B01L 3/00* (2006.01)
(52) U.S. Cl.
CPC ..... *B01L 3/5085* (2013.01); *B01L 2300/0829* (2013.01)

(58) Field of Classification Search
CPC .......... B01L 3/5085; B01L 2300/0829; B01L 2300/021; B01L 2300/0858; B01L 2300/168; B01L 3/545; C12M 23/12
See application file for complete search history.

(56) References Cited

U.S. PATENT DOCUMENTS 9,802,196 B2 * 10/2017 Taunk ................. B01L 3/50825
2007/0292837 A1 * 12/2007 Deutsch ................ B01L 3/5085
435/4

(Continued)

FOREIGN PATENT DOCUMENTS

CN     202621192 U   12/2012
CN     105505745 A    4/2016

(Continued)

OTHER PUBLICATIONS

Communication with Supplementary European Search Report, EP Application No. 16908901.8, dated Dec. 17, 2019, 7 pp.

(Continued)

*Primary Examiner* — Jill A Warden
*Assistant Examiner* — Sophia Y Lyle
(74) *Attorney, Agent, or Firm* — Myers Bigel, P.A.

(57) ABSTRACT

A multi-well plate allows for improvement in accuracy of experiments or tests. The present invention relates to a multi-well plate comprising: a top portion placed in a horizontal direction; a bottom portion opposing the top portion in a direction crossing the horizontal direction; and wells each recessed from the top portion toward the bottom portion, wherein the wells are horizontally arranged in a matrix with rows and columns, and each well has an opening formed at the top portion, and a peripheral wall extending from a periphery of the opening to the bottom portion. In the multi-well plate, at least two wells respectively include marks each containing at least one symbol, and each mark (Continued)

is placed at an opening peripheral wall end portion close to the corresponding opening.

7 Claims, 5 Drawing Sheets

(56) References Cited

U.S. PATENT DOCUMENTS

| | | | |
|---|---|---|---|
| 2014/0162351 | A1 | 6/2014 | Yamamoto et al. |
| 2016/0015598 | A1 | 1/2016 | Provencher et al. |

FOREIGN PATENT DOCUMENTS

| | | | | |
|---|---|---|---|---|
| CN | 205133583 U | 4/2016 | | |
| DE | 20211509 U1 | * 12/2003 | | B01L 3/5085 |
| DE | 20211509 U1 | 2/2004 | | |
| EP | 2539073 A1 | 1/2013 | | |
| JP | 2-25029 U | 2/1990 | | |
| JP | 8-114596 A | 5/1996 | | |
| JP | 08114596 A | * 5/1996 | | |
| JP | 3063248 U | 8/1999 | | |
| JP | 2004-150807 A | 5/2004 | | |
| WO | 2011/101467 A1 | 8/2011 | | |
| WO | WO 2013/030940 A1 | 3/2013 | | |

OTHER PUBLICATIONS

International Search Report with English language translation, International Application No. PCT/JP2016/083522, dated Jan. 31, 2017, 5 pp.

Written Opinion of the International Searching Authority, International Application No. PCT/JP2016/083522, dated Jan. 31, 2017, 3 pp.

"First Office Action and English language translation", CN Application No. 201680087433.2, dated Oct. 19, 2020, 14 pp.

* cited by examiner

MULTI-WELL PLATE

RELATED APPLICATIONS

This application is a 35 U.S.C. § 371 national stage application of PCT Application No. PCT/JP2016/083522, filed on Nov. 11, 2016, which claims priority from Japanese Patent Application No. 2016-140573, filed on Jul. 15, 2016, the contents of which are incorporated herein by reference in their entireties. The above-referenced PCT International Application was published in the English language as International Publication No. WO 2018/012002 A1 on Jan. 18, 2018.

TECHNICAL FIELD

The present invention relates to a multi-well plate having a plurality of recess-shaped wells.

BACKGROUND ART

In some experiments or tests in a field, such as chemistry, biology, or the like, multi-well plates of which each has a plurality of recess-shaped wells, are used. Each well of the multi-well plate serves, for example, as a test tube, a petri dish, or the like. In particular, multi-well plates are frequently used to simultaneously analyze multiple specimens in analytical tests in a field, such as biochemistry, medical science, or the like. The multi-well plate may also be called a microtiter plate, a microplate, or the like.

Typically, the multi-well plate has an outer shape formed in a rectangular when seen in a plan view, and the plurality of wells in the multi-well plate are arranged in a matrix with a plurality of rows which extend parallel to the long sides of the outer shape, and a plurality of columns which extend parallel to the short sides of the outer shape. An edge portion extending along one of the short sides of the multi-well plate (referred to as "short-side edge portion" below) may be provided with a plurality of symbols respectively indicating the plurality of rows, and an edge portion extending along one of the long sides of the multi-well plate (referred to as "long-side edge portion" below) may be provided with a plurality of symbols respectively indicating the plurality of columns.

In many cases, multi-well plates are made of plastic, and are manufactured by injection molding using a mold that can open and close so as to move in the recess direction of the wells. Samples contained in a multi-well plate, may be analyzed by a spectroscopic method using light absorption, fluorescence, or light emission. For such analysis, the samples in the wells may be irradiated through the bottom walls of the wells with light emitted by an analytical instrument, such as a multi-well plate reader. In this case, it is required to prevent interference of light, such as scattering, absorption, or the like, which has an influence on measurement errors, from occurring when the light passes through the bottom walls of the wells. To avoid such interference, it is demanded to manufacture the bottom walls of the wells so as to be free from colored elements that would block the passage of light. Therefore, considering that the mold opens and closes in the recess direction of the wells during injection molding and that prevention of interference of light such as scattering or absorption is required during analysis, a multi-well plate may be manufactured using a transparent resin material, and furthermore, either the bottom wall of each well or a portion, surrounding each well, of the top surface of the multi-well plate, may include one or more punch stamped symbols identifying the row and column that contain the well.

An example of such a multi-well plate may have 96 wells arranged in a matrix with eight rows and twelve columns, and may be provided with the alphabet letters "A" to "H" that are respectively defined as identifiers for the eight rows and are placed in the short-side edge portion, and the Arabic numerals "1" to "12" that are respectively defined as identifiers for the twelve columns and are placed in the long-side edge portion. In some cases, in an example multi-well plate, symbols that identify the row and column containing a well, may be punch stamped to the bottom wall of the well. In some cases, symbols that identify the row and column containing a well, may be punch stamped to a portion, surrounding the well, of the top surface of the multi-well plate (see Patent Documents 1 and 2, for example).

CITATION LIST

Patent Documents

Patent Document 1: JP H08-114596 A
Patent Document 2: JP 2004-150807 A

SUMMARY OF INVENTION

Technical Problem

Typically, an operator previously prepares a table or the like that specifies which samples are to be contained in the wells of the multi-well plate respectively. With reference to this table or the like, the operator manually then inputs samples in the wells using a micropipette and/or the like. In some large-scale experiments or tests, samples may be input in a multi-well plate generally using a machine called a pipettor, but initially, manually input in the above manner. In a laboratory scale experiment or test, samples are also manually input in a multi-well plate in the above manner.

Here, the above multi-well plate requires an experiment or test operator who wishes to input a sample into a target well, to first move the line of sight onto at least one of the symbols provided in the short-side and long-side edge portions before directing the line of sight to the target well.

Furthermore, when the symbols for each well are punch stamped to the bottom wall of the well in the above multi-well plate, the operator who wishes to read the symbols, is required to view the wells from vertically above. However, when, for example, an operator handles the multi-well plate that is placed in a clean bench and/or the like, it is difficult for the operator to work in a position that provides a vertical top view of the wells. For this reason, typically, the operator works in a position that provides only an oblique top view of the wells. This makes it difficult for the operator to view and read the symbols in the bottom walls of the wells. A conceivable measure to address this problem may be tilting the position of the multi-well plate so as to offer the operator the ease of viewing the symbols that are provided in the bottom walls of the wells respectively. However, in this situation, the samples may spill out of the wells, uneven sample density distribution among the wells may occur, and as a result, work, such as analysis and/or the like, may be difficult. Furthermore, the punch stamped symbols naturally have the transparent color in the same manner as the bottom walls of the wells, and this makes it significantly difficult to identify the symbols. In addition, after the samples are contained in the wells, the samples make it more difficult to view the bottom walls of the wells.

On the other hand, when the symbols for each well are punch stamped to a portion, surrounding the well, of the top surface of the multi-well plate as described above, the symbols are located between adjacent wells on the top surface of the multi-well plate. This makes it difficult for an operator to determine which one of these adjacent wells is indicated by the symbols.

As a result, the operator using the multi-well plate, may misidentify a non-target well as a target well, even though a sample to be input to the non-target well is different from a sample to be input to the target well. In particular, when the multi-well plate has a plurality of wells that are regularly arranged in a matrix so as to repeat the same pattern, such a risk of misidentification increases. Such misidentification among wells further leads to a risk of inputting an incorrect sample into a well, and the contamination by foreign matter, such as an incorrect sample, in a well reduces the accuracy of the experiment or test.

In view of the above, there is a demand to prevent the contamination by foreign matter, such as an incorrect sample and/or the like, in wells, and thereby to improve the accuracy of experiment or test using a multi-well plate. In addition, much time has been conventionally spent in identifying which well is a current target well for sample input. Thus, there is another demand for reduction of time required to such target well identification so as to reduce work time for completing the experiment or test. In other words, there is a demand to improve the workability in the experiment or test using the multi-well plate.

Solution to Problem

To solve the above problems, a multi-well plate according to an aspect of the present invention comprises: a top portion placed in a horizontal direction; a bottom portion opposing the top portion in a direction crossing the horizontal direction; and a plurality of wells of which each is formed so as to be recessed from the top portion toward the bottom portion, wherein the plurality of wells are horizontally arranged in a matrix with a plurality of rows and a plurality of columns, each of the wells has an opening formed at the top portion, and a peripheral wall extending from a periphery of the opening to the bottom portion, at least two of the plurality of wells respectively include marks of which each contains at least one symbol, and each of the marks is placed at an opening peripheral wall end portion of a corresponding one of the peripheral walls, each opening peripheral wall end portion being located close to a corresponding one of the openings.

Advantageous Effects of Invention

The multi-well plate according to an aspect of the present invention allows for improving the workability in an experiment or test.

DESCRIPTION OF EMBODIMENTS

Multi-well plates according to First to Fourth Embodiments of the present invention will be described below. In FIGS. 1 to 9 for explaining the First to Fourth Embodiments of the present invention, a proximal direction which is toward an operator using the multi-well plate, is indicated by arrow P, and a distal direction which is away from the operator, is indicated by arrow D. That is to say, in each Embodiment, it is assumed that the operator is positioned closer to the direction indicated by arrow P than the multi-well plate, and uses the multi-well plate with an oblique top view of the multi-well plate. However, the present invention is not limited to this, and an operator may use the multi-well plate while being positioned closer to a direction other than that indicated by arrow P, than the multi-well plate.

Furthermore, in each Embodiment, it is considered that the operator uses the multi-well plate while viewing a target well with the operator's eyes approximately 10 cm to approximately 50 cm away proximally from the target well and approximately 20 cm to approximately 60 cm away above the opening of the target well. In such viewing conditions, the angle of the line of sight of the operator is approximately 45 degrees to approximately 72 degrees with respect to the horizontal direction. Furthermore, in each Embodiment, it is considered that, when the operator inputs a sample into a target well, the operator uses the multi-well plate while viewing the target well with the operator's eyes approximately 15 cm to approximately 30 cm away proximally from the target well and approximately 30 cm to approximately 45 cm away above the opening of the target well. In such viewing conditions, the angle of the line of sight of the operator is approximately 50 degrees to approximately 60 degrees with respect to the horizontal direction. However, the present invention is not limited to the above, and an operator may use the multi-well plate under viewing conditions other than the above viewing conditions.

First Embodiment

A multi-well plate according to a First Embodiment of the present invention will be described below.

Outline of Multi-Well Plate

Figure 1:
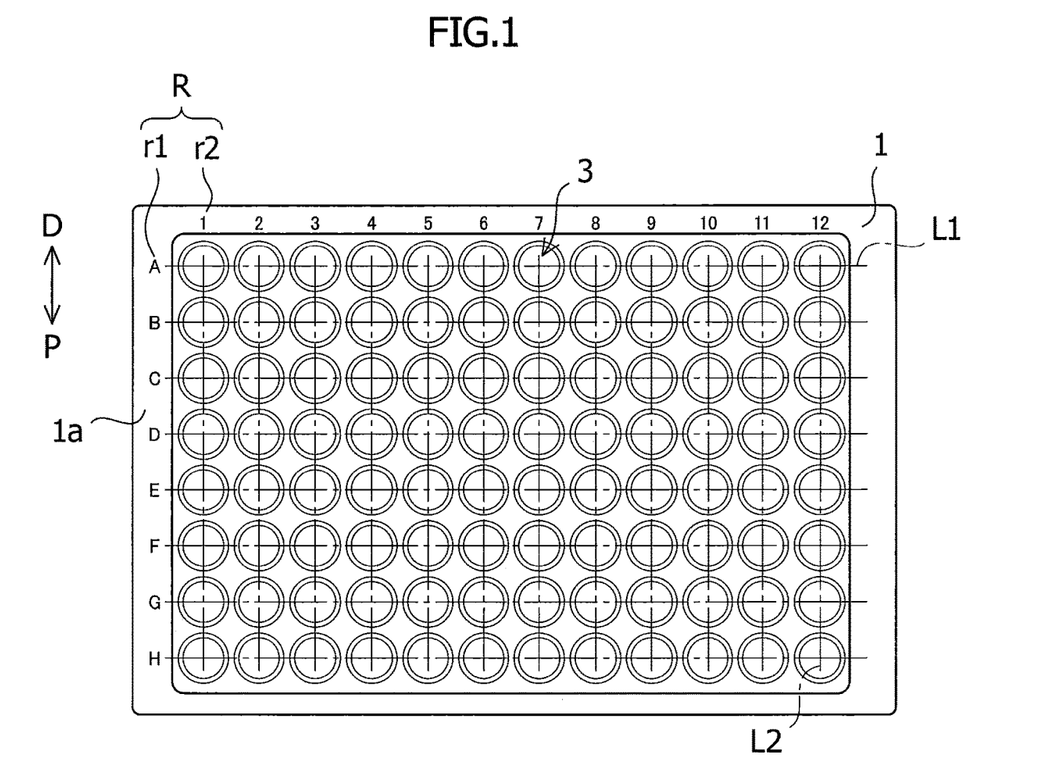
FIG. 1 is a plan view schematically showing a multi-well plate according to a First Embodiment of the present invention.
Figure 2:
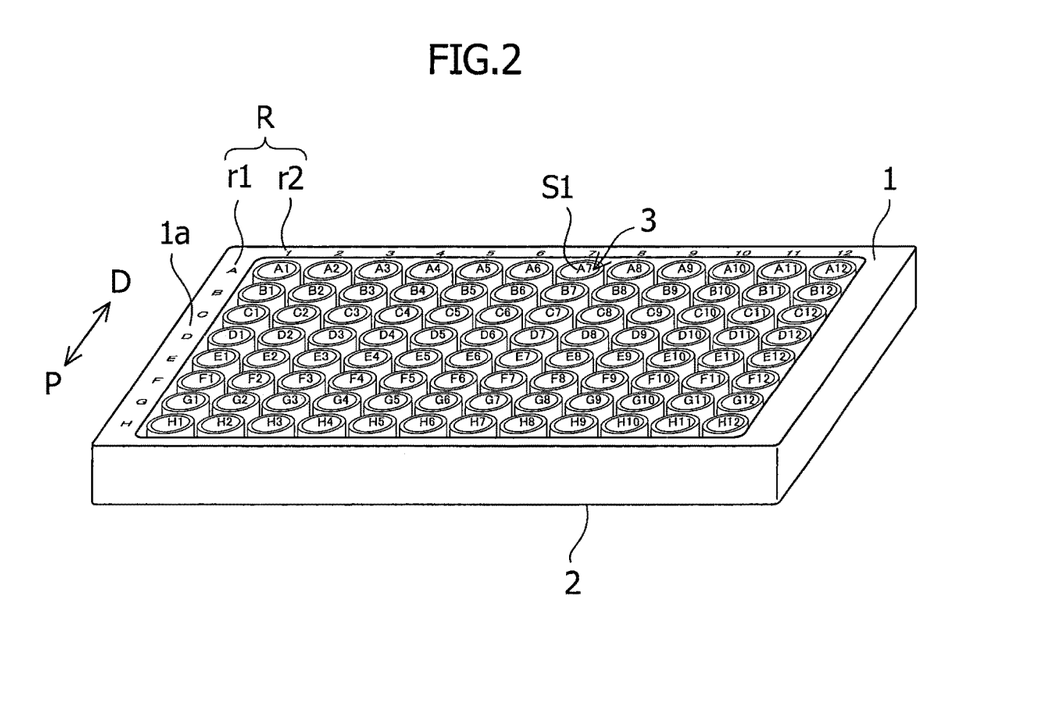
FIG. 2 is a perspective view schematically showing the multi-well plate according to the First Embodiment of the present invention.

First, the outline of the multi-well plate will be described. As shown in FIGS. 1 and 2, the multi-well plate includes: a top portion 1 placed in the horizontal direction; a bottom portion 2 opposing the top portion 1 in a direction crossing the horizontal direction (referred to as "crossing direction" below); and a plurality of wells 3 of which each is formed so as to be recessed from the top portion 1 toward the bottom portion 2. As defined herein, the operator-proximal direction which is indicated by arrow P, is one of the opposing sides of a first directional element included in the horizontal direction, and the operator-distal direction which is indicated by arrow D, is the other of the opposing sides of the first directional element. As shown in FIG. 2, the above crossing direction is substantially perpendicular to the horizontal direction.

As shown in FIGS. 1 and 2, each well 3 is recessed in a direction substantially perpendicular to the horizontal direction. In addition, the plurality of wells 3 are surrounded by an outer peripheral region 1*a* of the top portion 1. The outer peripheral region 1*a* has a plurality of edge marks R of which each contains at least one symbol. Furthermore, as shown in FIG. 2, each of the wells 3 has a well mark S1 containing at least one symbol. Such a multi-well plate may preferably be made of a material, such as a plastic, glass, metallic material, and/or the like. For example, the plastic material may contain polyethylene, polypropylene, polystyrene, ABS resin, polycarbonate, polyamide, PMMA, and/or the like. In this Embodiment, the multi-well plate is substantially transparent, and the wells 3 have substantially the same color with each other.

As shown again in FIGS. 1 and 2, the outer shape of the multi-well plate, in particular, the outer shape of the top portion 1, is substantially quadrilateral in a plan View. In this case, the outer shape of the multi-well plate includes a pair of first sides extending parallel to the first directional element, and a pair of second sides extending parallel to a second directional element which substantially perpendicular to the first directional element.

However, the present invention is not limited to the above, and the outline of the multi-well plate may alternatively be configured as follows. The crossing direction does not have to be substantially perpendicular to the horizontal direction, and may be oblique to the horizontal direction. Each well may be recessed in a direction oblique to the horizontal direction. The outer peripheral region of the top portion does not include edge marks. The outer peripheral region of the top portion may be partially or entirely omitted from the multi-well plate. In this case, some or all of the wells located at the outermost periphery of the multi-well plate may be arranged along its outer peripheral surface, and some or all of the edge marks may be omitted. The multi-well plate may be configured such that all wells do not necessarily have to include well marks respectively, and, at least two of the wells can include well marks respectively.

In addition, the multi-well plate does not have to be substantially transparent, that is to say, the multi-well plate may be translucent or opaque. Alternatively, the multi-well plate may be configured such that the bottom wall, which will be described later, of each well is transparent and the remaining portion of each well other than the bottom wall is opaque. Still alternatively, the multi-well plate may be configured such that the bottom wall of each well is transparent and the peripheral wall, which will be described later, of each well has a color that is able to prevent light transmission, such as white, black, and/or the like. The outer shape of the multi-well plate, in particular, the outer shape of the top portion, may be formed in a shape other than substantially quadrilateral in a plan view. Furthermore, some of the plurality of wells may be colored differently from others of the plurality of wells.

Details of Wells

Next, the details of the wells 3 will be described. As shown in FIG. 1, in the multi-well plate, the plurality of wells 3 are horizontally arranged in a matrix with a plurality of rows and a plurality of columns. In the matrix, each of the rows is arranged on a straight line L1 (indicated by dashed-dotted line) extending parallel to the second directional element, and each of the columns is arranged on a straight line L2 (indicated by dashed-dotted line) extending parallel to the first directional element.

Specifically, as shown in FIGS. 1 and 2, the wells 3 are horizontally arranged in a matrix with n rows and m columns. Thus, each row contains m wells 3 and each column contains n wells 3. In this case, the multi-well plate has n×m wells 3. Here, each of n and m may be an integer of 2 or more, in particular, an integer of 3 or more. For example, the number of wells arranged in a matrix may be 6, 12, 24, 48, 96, 384, 1536, or the like. In particular, in view of the necessity of preventing misidentification among a large number of wells, the number of wells arranged in a matrix may preferably be 12, 24, 48, 96, 384, or 1536. Furthermore, in view of the necessity of preventing misidentification between a large number of wells, and view of the objective of allowing each well mark to have a visually recognizable size, the number of wells arranged in a matrix may more preferably be 12, 24, 48, 96, or 384. Each row is given at least one symbol so as to identify the n rows separately from one another. Each column is given at least one symbol so as to make the m columns separately from one another.

As an example, in FIGS. 1 and 2, 96 wells 3 are arranged in a matrix with eight rows and twelve columns. The eight different rows are given different symbols "A" to "H" so as to identify the rows separately from one another. The twelve different columns are given different symbols "1" to "12" so as to identify the columns separately from one another. As the individual edge marks R, the symbols of "A" to "H" and symbols "1" to "12" are displayed on the multi-well plate.

Figure 3:
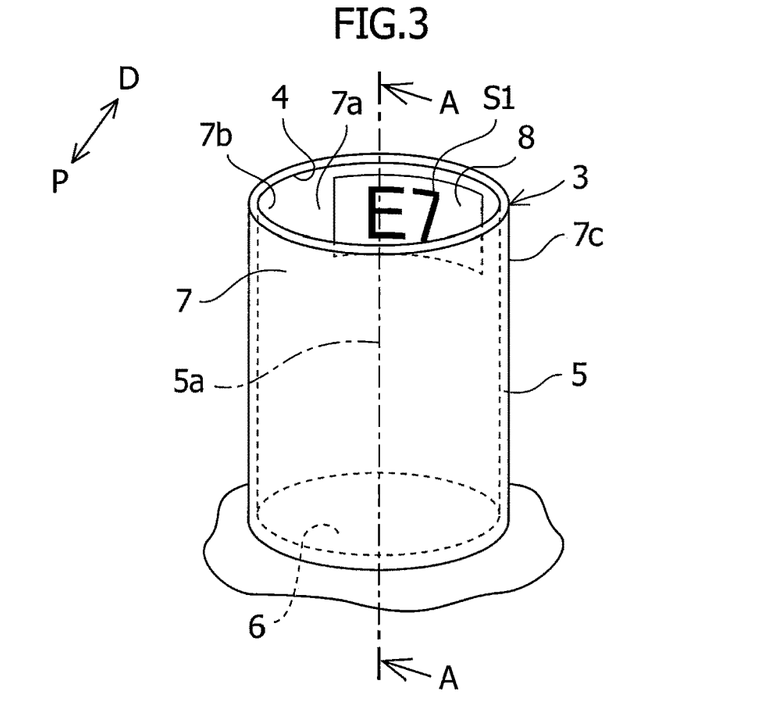
FIG. 3 is an enlarged perspective view schematically showing a well in the multi-well plate according to the First Embodiment of the present invention, as viewed from an operator-proximal side.
Figure 4:
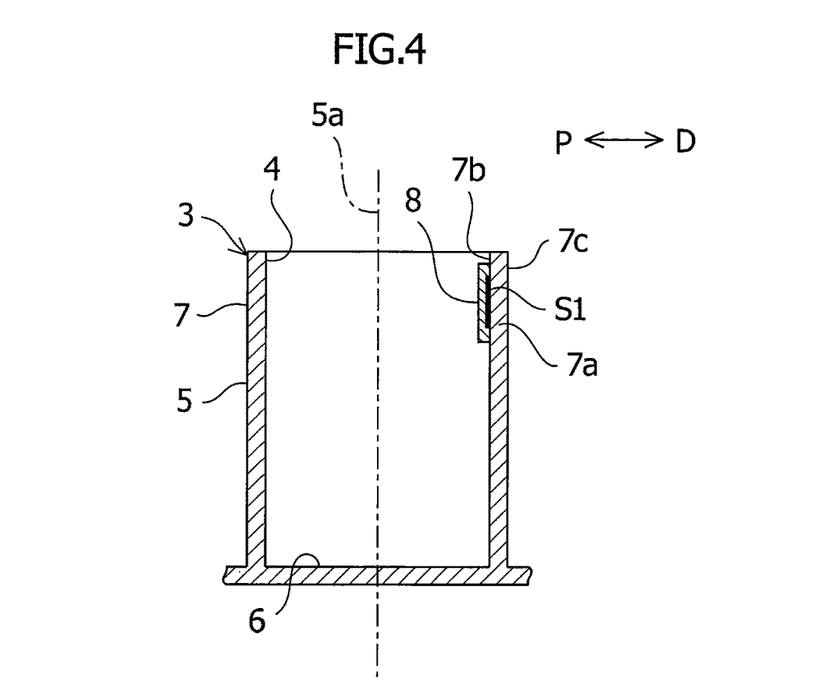
FIG. 4 is a cross-sectional view taken along line A-A of FIG. 3.

As shown in FIGS. 3 and 4, each well 3 has: an opening 4 formed at the top portion 1; a peripheral wall 5 extending from the periphery of the opening 4 to the bottom portion 2; sand a bottom wall 6 that faces the opening 4 in the crossing direction. The peripheral wall 5 is formed in a tube shape extending between the opening 4 and the bottom wall 6. As shown in FIG. 3, the opening 4 of the well 3 is formed in a substantially circular shape, and the peripheral wall 5 of the well 3 is formed so as to have a substantially circular transverse cross section corresponding to the shape of the opening 4. As shown in FIG. 4, the bottom wall 6 of the well 3 is formed in a substantially flat shape.

As shown in FIGS. 2 to 4, the well mark S1 is placed on an opening peripheral wall end portion 7, which is located close to the opening 4 of the well 3, of the peripheral wall 5. Furthermore, with the objective of offering the operator the ease of viewing the well mark S1, it is preferable to place the well mark S1 on a distal region 7*a* of the opening peripheral wall end portion 7. Here, the distal region 7*a* is located closer to operator-distal than a central axis 5*a* (indicated by the dashed-dotted line) of the peripheral wall 5.

The ratio of the height of the opening peripheral wall end portion 7 to the height of the well 3 may be set such that the operator who views the multi-well plate under the above viewing conditions, can read the well marks S1 of which each is placed on the corresponding opening peripheral wall end portion 7, through the openings 4, and a space for placing the well mark S1 can be secured. In particular, in view that the operator who views the multi-well plate under the above viewing conditions, can read the well marks S1 of which each is placed on the corresponding opening peripheral wall end portion 7, through the openings 4, the ratio may preferably be approximately 0.5 or less, and particularly preferably be approximately 0.4 or less. On the other hand, in view that a space for placing each well mark S1, can be secured, the ratio may preferably be approximately 0.1 or more, and may particularly preferably be approximately 0.2 or more. Each well mark S1 is placed on the opening peripheral wall end portion 7 within such a range in its height direction. In view of offering the operator the ease of identifying the well marks S1, when the multi-well plate is transparent, translucent, or light colored, the color of the well marks S1 may preferably be darker than that of the multi-well plate. For example, the color of the well marks S1 may be black, brown, dark blue, violet, or the like. The well marks S1 placed in all the wells 3, have substantially the same color.

However, the present invention is not limited to the above, and the details of the wells may alternatively be the following. The plurality of wells may be arranged in a pattern other than a matrix. For example, the number of wells contained in each of some of the columns may be different from the number of wells contained in each of others of the plurality of columns. Regarding the directions of the rows and columns of the wells, if the direction in which the rows extend, is substantially perpendicular to the direction in which the columns extend, the rows may extend in a direction not parallel to the second directional element, and the columns may extend in a direction not parallel to the first directional element.

Furthermore, at least one of the opening and the transverse cross section of the peripheral wall of each well may be formed into a shape other than a substantially circular shape. For example, at least one of the opening and the transverse cross section of the peripheral wall of each well may have a substantially polygonal shape, such as a substantially quadrilateral shape. The bottom wall of each well may be formed into a shape other than a substantially flat shape. For example, the bottom wall of the well may be substantially curved, substantially bent, substantially conical, substantially pyramidal, or the like. Each well may additionally have a through hole formed in a portion other than the opening. For example, a through hole may be formed at a part or the whole of the bottom of the well, or the bottom wall of the well may be porous. In each row or each column of the wells, wells with the well marks and wells without the well marks may be arranged alternately. As long as each well mark is placed on one region of opening peripheral wall end portion, which is located closer to one-way of a directional element of the horizontal direction than the central axis of the peripheral wall, and each well can be placed on a region other than the distal region of the opening peripheral wall end portion.

In addition, when the multi-well plate has a dark color, the color of the well marks may be lighter than that of the multi-well plate. In this case, the color contrast between the well marks and the multi-well plate may preferably be at a level that allows the operator to identify the well marks. For example, the color of the well marks may be white, yellow, or the like. Furthermore, the color of the well marks placed in some of the wells, may differ from the color of the well marks placed in others of the wells.

Details of Edge Marks

Next, the details of the edge marks R will be described. As shown in FIGS. 1 and 2, the edge marks R are provided, using a colorant, onto the outer peripheral region 1a of the top portion 1 of the multi-well plate. The plurality of edge marks R include a plurality of row identification edge marks r1 that identify the n rows of wells 3 separately from one another, and a plurality of column identification edge marks r2 that identify the m columns of wells 3 separately from one another. Each row identification edge mark r1 contains at least one symbol which is given to the corresponding row so as to identify the n rows separately from one another. Each column identification edge mark r2 contains at least one symbol which is given to the corresponding column so as to identify the m columns separately from one another.

As an example, in FIGS. 1 and 2, the eight different row identification edge marks r1 contain different symbols of alphabet letters "A" to "H" so as to identify the eight rows separately from one another. The twelve different column identification edge marks r2 contain different symbols of Arabic numerals "1" to "12" so as to identify the twelve columns separately from one another.

As shown in FIG. 1, the plurality of row identification edge marks r1 are respectively placed on the plurality of the straight lines L1 extending along the n rows. The plurality of column identification edge marks r2 are respectively placed on the plurality of the straight lines L2 extending along the m columns. The plurality of row identification edge marks r1 are located on a side closer to one-way of the second directional element than the plurality of wells 3, and are lined up parallel to the first directional element. The plurality of column identification edge marks r2 are located on a side closer to one-way of the first directional element than the plurality of wells 3, and are lined up parallel to the second directional element.

As an example, in FIG. 1, eight row identification edge marks r1 are respectively placed on the eight straight lines L1 extending along the eight rows, and twelve column identification edge marks r2 are respectively placed on the twelve straight lines L2 extending along the twelve columns. The eight row identification edge marks r1 are located on a side closer to one-way of the second directional element than the 96 wells 3, in particular, on the left side as viewed from the operator, with respect to the 96 wells 3. The eight row identification edge marks r1 are arranged such that their symbols "A", "B", "C", "D", "E", "F", "G", and "H" are arranged in this order in a direction from the operator-distal side to the operator-proximal side. The twelve column identification edge marks r2 are located on a side closer to one-way of the first directional element than the wells 3, in particular, on the operator-distal side with respect to the wells 3. The twelve column identification edge marks r2 are arranged such that their symbols "1", "2", "3", "4", "5", "6", "7", "8", "9", "10", "11", and "12" are arranged in this order in a direction from the left side to the right side as viewed from the operator.

However, the present invention is not limited to the above, and the details of the edge marks may alternatively be the following. The edge marks is provided onto at least one sheet member with a colorant, and the at least one sheet member is attached onto the outer peripheral region so that the edge marks may be provided onto the outer peripheral region of the top portion of the multi-well plate. Alternatively, the edge marks may be provided onto the outer peripheral region of the top portion by color change or removal in at least a portion of the outer peripheral region of the top portion with laser marking. Still alternatively, the edge marks may be punch stamped to the outer peripheral region of the top portion of the multi-well plate. In particular, when the plurality of wells are not arranged in a matrix, the at least one symbol contained in each edge mark, may be: a character, such as an Arabic numeral, a Japanese hiragana, katakana, or kanji character, a letter of the alphabet, a Greek letter, a Hangul character, an Arabic letter, or the like; a graphic; or the like, which is not the above symbol identifying the corresponding row or column from among the n rows or the m columns.

Symbols in Well Marks

Next, the symbols of the well marks S1 will be described. As shown in FIGS. 1 and 2, the well mark S1 provided in each well 3, has at least one symbol that identifies the row containing the well 3, and at least one symbol that identifies the column containing the well 3. Each of the well marks S1 provided in all the plurality of wells 3, includes symbols having such a correspondence relationship.

In the well mark S1 provided in each well 3, the at least one symbol that identifies the row containing the well 3, and the at least one symbol that identifies the column containing the well 3 are arranged side by side in the circumferential direction of the peripheral wall 5. As viewed from the operator, the at least one symbol that identifies the row is located on the left, and the at least one symbol that identifies the column is located on the right. The number of such symbols contained in each well mark S1, may preferably be from one to four, inclusive. Regarding the relationship between the height and width of the font used for each symbol of the well mark S1, the height may preferably be greater than the width, and more preferably, the ratio of the width to the height may be within the range of approximately 1.4 to approximately 3, inclusive. The font of each symbol of the well mark S1 may preferably be Gothic.

As an example, in FIGS. 1 and 2, each of the well marks S1 provided in the wells 3, has one of the symbols "A" to "H" that identifies the row containing the corresponding well 3, and one of the symbols "1" to "12" that identifies the column containing the well 3. Each of the well marks S1 provided in all the 96 wells 3, has symbols having such a correspondence relationship. For example, as shown in FIGS. 2 and 3, the well mark S1 of the well 3 that is contained in the row identified by the symbol "E" and contained in the column identified by the symbol "7", has the symbols "E" and "7". In this case, the well mark S1 of this well 3 is displayed as "E7".

However, the present invention is not limited to the above, and the details of the symbols of the well marks may alternatively be the following. All the well marks provided in all the plurality of wells, do not necessarily have to include the symbols having the above correspondence relationship, and the well marks provided in only at least two of the wells, can include the symbols having the above correspondence relationship. In particular, when the plurality of wells are not arranged in a matrix, the at least one symbol provided in each well, may be: a character, such as an Arabic numeral, a Japanese hiragana, katakana, or kanji character, a letter of the alphabet, a Greek letter, a Hangul character, an Arabic letter or the like; a graphic; or the like, which is not the symbol identifying the corresponding row and column from among the n rows and m columns.

Furthermore, in the well mark of each well, the at least one symbol that identifies the row containing the well, may be located on the right, and the at least one symbol that identifies the column containing the well, may be located on the left, as viewed from the operator. Alternatively, in the well mark of each well, the at least one symbol that identifies the row containing the well, and the at least one symbol that identifies the column containing the well, may be arranged side by side in a direction other than the circumferential direction of the peripheral wall. For example, the at least one symbol that identifies the row containing the well, and the at least one symbol that identifies the column containing the well, may be arranged side by side in the height direction of the well.

In addition, regarding the relationship between the height and width of the font used for each symbol of the well mark, the height may be smaller than the width. Furthermore, the ratio of the width to the height may be outside the range, inclusive, of approximately 1.4 to approximately 3. The font of each symbol contained in the well mark S1, does not necessarily have to be Gothic, and may be a Ming style, Kaisyo (regular) style, Gyosho (semi-cursive) style font, or the like. The number of symbols contained in each well mark, may be five or more.

Here, the use of two or more symbols may sometimes be required to identify each row, and/or the use of two or more symbols may sometimes be required to identify each column. In such a case, only one of these required two or more symbols may be displayed in a font that is changed so as to represent the remaining of these two or more symbols. For example, when a well mark is required to indicate "12" for identifying the column containing the corresponding well, only "2", which is one of the digits of "12", may be displayed in a changed font such as a bold font, a blackboard bold, a composite font, underlined font, or the like. As an alternative measure to achieve the same objective, "2" may be displayed in a changed color or in a changed font size.

Placement of Well Marks

Next, the placement of the well marks S1 will be described. As shown in FIGS. 3 and 4, each well mark S1 is formed with a colorant and is placed along an inner peripheral surface 7b of the opening peripheral wall end portion 7 in the corresponding well 3. Specifically, the well mark S1 is provided, with a colorant, onto the inner peripheral surface 7b of the opening peripheral wall end portion 7 of the corresponding well 3, which is previously formed.

The colorant may be depositable onto the inner peripheral surface 7b of the opening peripheral wall end portion 7. In particular, the color matters contained in the colorant, may preferably be water-insoluble. For example, the color matters contained in the colorant, may be solvatochromic color matters or other color matters which have water-sensitive color characteristics. In this case, it is easy to identify between wells 3 with the well marks S1 of which each has color characteristics before sample input, and wells 3 with the well marks S1 of which each has characteristics changed by sample input.

The well marks S1 are also covered with a coating element 8 that is made of a substantially transparent coating material. In particular, the coating material may preferably be a resin material. The coating element 8 is formed on the inner peripheral surface 7b by applying the coating material onto the inner peripheral surface 7b of the opening end portion 7 of the peripheral wall 5.

However, the present invention is not limited to the above, and the placements of the well marks onto the multi-well plate may alternatively be the following. As long as each well mark is formed using a colorant and is placed along the inner peripheral surface of the opening peripheral wall end portion in the corresponding well, the well mark may be provided onto the coating element. The coating element may be a sheet member made of a substantially transparent coating material, and may be affixed onto the inner peripheral surface of the opening peripheral wall end portion. For example, when the coating element is a sheet member, a well mark may be provided onto an affixing surface of the coating element using a colorant, and the coating element may be affixed onto the inner peripheral surface of the opening peripheral wall end portion such that the affixing surface is in contact with the inner peripheral surface of the opening peripheral wall end portion. The coating element may be configured so as to cover, from the top of the multi-well plate, all or part of a top region, which includes the interiors of all the wells, of the multi-well plate. In this case, the coating element can be a transparent resin member or the like having a shape corresponding to the shape of all or part of the top region of the multi-well plate. Alternatively, the well marks may be formed integral with the wells using a 3D printer. In this case, the well marks do not necessarily have to be covered with the coating element. The wells having well marks, may be manufactured by shaping a member which has been previously provided with the well marks, into well shapes.

According to this Embodiment described above, the multi-well plate includes: the top portion 1 placed in the horizontal direction; the bottom portion 2 opposing the top portion 1 in a direction crossing the horizontal direction; and the plurality of wells 3 of which each is formed so as to be recessed from the top portion 1 toward the bottom portion 2. The plurality of wells 3 are horizontally arranged in a matrix with a plurality of rows and a plurality of columns. Each well 3 has the opening 4 formed in the top portion 1, and the peripheral wall 5 extending from the periphery of the opening 4 to the bottom portion 2. At least two of the plurality of wells 3 respectively include the well marks S1 of which each contains at least one symbol. Each of the well marks S1 is placed on the opening peripheral wall end portion 7 of the corresponding peripheral wall 5.

Accordingly, even if the multi-well plate of this Embodiment has the plurality of wells 3 that are regularly arranged in a matrix so as to repeat the same pattern, an experiment or test operator who wishes to input a predetermined sample into a target well 3, can easily view and recognize the well mark S1 which is provided on the opening peripheral wall end portion 7 of the exact target well 3. Furthermore, the multi-well plate also allows the operator to reliably input a predetermined sample into a target well 3 while keeping the line of sight on the well mark S1 which provided in the exact target well 3, and accurately identifying the target well 3 separately from the other wells 3. In addition, even after the samples have been contained in the wells 3, the operator can still easily view the well marks S1 provided on the opening peripheral wall end portions 7 of the wells 3 because the opening peripheral wall end portion 7 of each well 3 is generally located above the liquid level of the sample. This effectively prevents the contamination by foreign matter, such as an incorrect sample, in the wells. Furthermore, even when the samples in the wells 3 are irradiated through the bottom walls 6 of the wells 3 with light emitted by an analytical instrument, such as a multi-well plate reader, the well marks S1 will not interfere with the light. Therefore, the accuracy of experiments or tests using the multi-well plate, can be improved. In addition, time required to identify a target well 3, can be reduced, and thus, work time for completing the experiment or test using the multi-well plate, can be reduced. Accordingly, the workability in the experiment or test using the multi-well plate, can be improved.

In the multi-well plate according to this Embodiment, when at least one symbol is defined for each of the plurality of rows so as to identify the plurality of rows separately from one another, and at least one symbol is defined for each of the plurality of columns so as to identify the plurality of columns separately from one another, each of the well marks S1 respectively provided to at least two of the plurality of wells 3, contains the at least one symbol that identifies the row containing the corresponding well 3, and the at least one symbol that identifies the column containing the well 3. These well marks S1 of which each contains the at least one symbol identifying the row containing the corresponding well 3, and the at least one symbol identifying the column containing the well 3, allow the operator to input a predetermined sample into a target well 3 while keeping the line of sight on the target well 3 and accurately identifying the target well 3 separately from the other wells 3.

In the multi-well plate according to this Embodiment, each well mark S1 is placed on one region, located closer to one-way of the directional element of the horizontal direction than the central axis 5a of the peripheral wall 5, of the opening peripheral wall end portion 7, in particular, is placed on the distal region 7a of the opening peripheral wall end portion 7. Thus, when an operator uses the multi-well plate from a side positioned closer to the other-way of this directional element than the multi-well plate, in particular, from the operator-proximal side, the operator can easily catch sight of the one regions of the opening peripheral wall end portions 7, in particular, the distal regions 7a thereof, on which the well marks S1 are placed. This allows the operator to input a predetermined sample into a target well 3 while stably keeping the line of sight on the target well 3 and accurately identifying the target well 3 separately from the other wells 3.

In the multi-well plate according to this Embodiment, each well mark S1 is formed using a colorant, and is placed along the inner peripheral surface 7b of the opening peripheral wall end portion 7. This offers the ease of viewing the well marks S1. In addition, the well marks S1 are covered with a substantially transparent coating element. This prevents contact between the well marks S1 and the samples that are input in the wells 3, without compromising the ease of viewing the well marks S1 offered to the operator. Furthermore, such a covering is also able to prevent the colorant that constitutes the well marks S1, from peeling off and being mixed into the samples in the wells 3, and therefore, the accuracy of experiment or test using the multi-well plate, can be improved.

Second Embodiment

Next, a multi-well plate according to a Second Embodiment of the present invention will be described. The outline of the multi-well plate, the details of the wells, the details of the edge marks, and the symbols in the well marks in the multi-well plate according to this Embodiment are the same as those in the multi-well plate according to the First Embodiment. However, the placements of the well marks in the multi-well plate according to this Embodiment are different from those in the multi-well plate according to the First Embodiment. Below, the placements of the well marks in the multi-well plate according to this Embodiment will be described.

Placements of Well Marks

Figure 5:
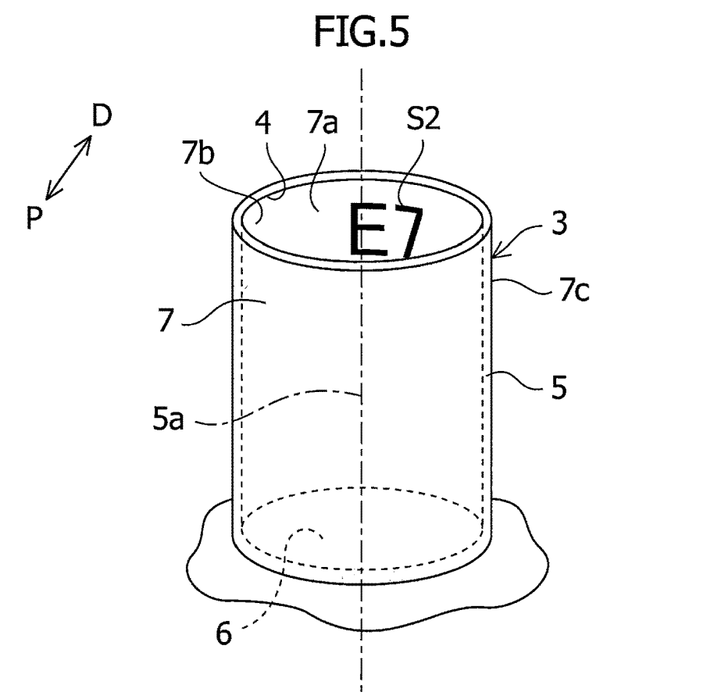
FIG. 5 is an enlarged perspective view schematically showing a well in a multi-well plate according to a Second Embodiment of the present invention, as viewed from the operator-proximal side.

With reference to FIG. 5, the placements of well marks S2 will be described. In the multi-well plate, each well mark S2 is provided onto the inner peripheral surface 7b of the opening peripheral wall end portion 7 of the peripheral wall 5 in the corresponding well 3 by color change or removal in at least a portion of the inner peripheral surface 7b of the opening peripheral wall end portion 7 with laser marking.

In the laser marking, each of the previously-formed inner peripheral surfaces 7b of the opening peripheral wall end portions 7 is irradiated with a laser beam so that heat generated by such laser irradiation, causes a chemical change in the shape of the corresponding well mark S2. This chemical change results in a color change in the shape of the well mark S2 in at least a portion of the inner peripheral surface 7b. In this way, the well marks S2 are provided onto the inner peripheral surfaces 7b of the opening peripheral wall end portions 7. When the above method is used to provide the well marks S2, the multi-well plate may preferably be made of a laser-markable material, such as a laser-markable plastic, metallic material, or the like. Examples of the laser-markable plastic material may include a plastic material that contains ABS resin, polycarbonate, polyamide, PMMA, or the like, and a plastic material that contains a laser additive. However, the present invention is not limited to the above. The wells having well marks, may be manufactured by shaping, into well shapes, a member previously provided with the well marks by laser marking.

The multi-well plate according to this Embodiment described above is able to provide the same advantages and effects as those provided by the multi-well plate according to the First Embodiment, except for the advantages and effects based on the placements of the well marks S1.

Furthermore, in the multi-well plate according to this Embodiment, each well mark S2 is provided onto the inner peripheral surface 7b of the opening peripheral wall end portion 7 by causing color change or removal in at least a portion of the inner peripheral surface 7b of the opening peripheral wall end portion 7 with laser marking. Accordingly, the well mark S2 is formed as a portion chemically changed by the laser marking in the plastic material of the multi-well plate. This results in less foreign matter production due to the provision of the well marks S2. Thus, the multi-well plate according to this Embodiment is able to prevent foreign matter, such as a material from the well marks S2, from being mixed into the samples in the wells 3, and improve the accuracy of experiment or test using the multi-well plate.

Third Embodiment

Next, a multi-well plate according to a Third Embodiment of the present invention will be described. The outline of the multi-well plate, the details of the wells, the details of the edge marks, and the symbols in the well marks in the multi-well plate according to this Embodiment are the same as those in the multi-well plate according to the First Embodiment. However, the placements of the well marks in the multi-well plate according to this Embodiment are different from those in the multi-well plate according to the Third First Embodiment. Below, the placements of the well marks in the multi-well plate according to this Embodiment will be described.

Placements of Well Marks

Figure 6:
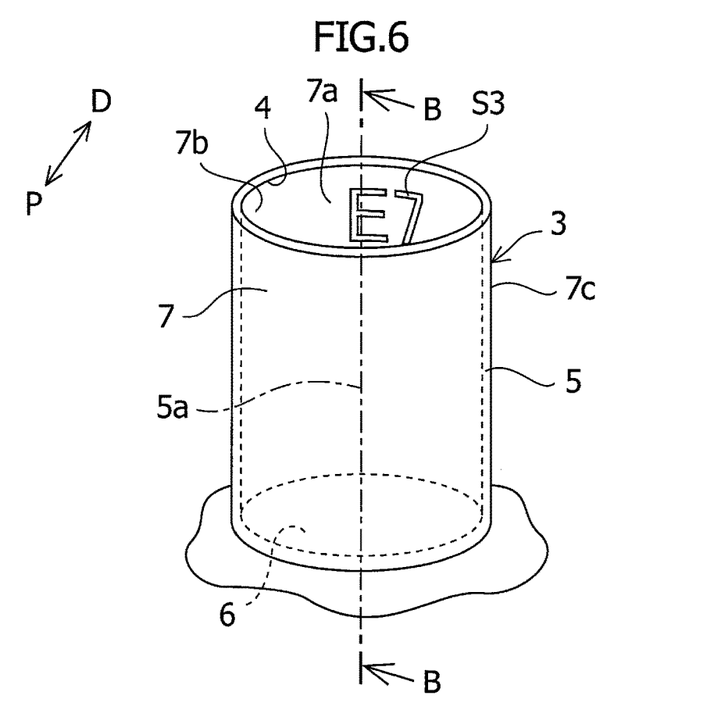
FIG. 6 is an enlarged perspective view schematically showing a well in a multi-well plate according to a Third Embodiment of the present invention, as viewed from the operator-proximal side.
Figure 7:
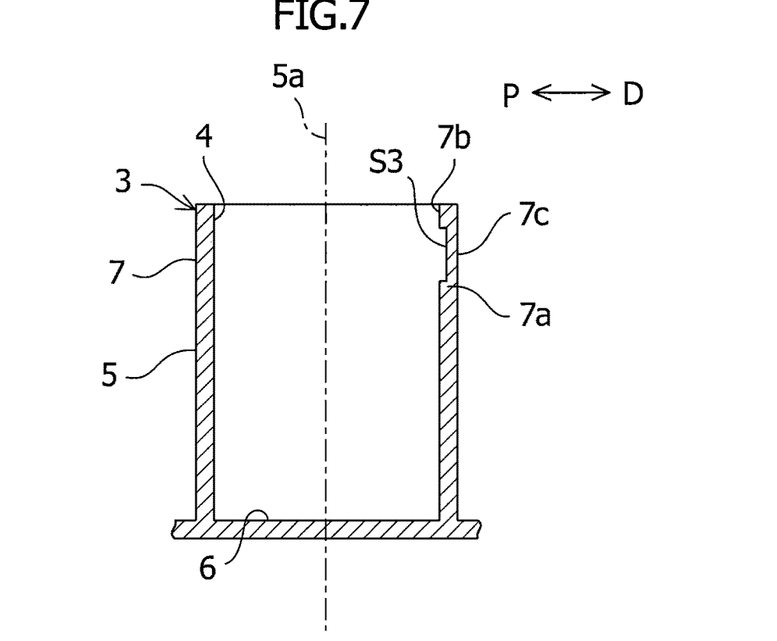
FIG. 7 is a cross-sectional view taken along line B-B of FIG. 6.

With reference to FIGS. 6 and 7, the placements of well marks S3 will be described. In the multi-well plate, each well mark S3 is punch stamped to the inner peripheral surface 7b of the opening peripheral wall end portion 7 in the corresponding well 3. The well mark S3 is formed so as to be recessed from the inner peripheral surface 7b of the opening peripheral wall end portion 7. Specifically, the well mark S3 is formed by scraping a portion of the previously formed well 3 with a laser marker.

However, the present invention is not limited to the above, and the placements of the well marks in the multi-well plate may alternatively be the following. The well mark may be formed so as to protrude from the inner peripheral surface of the opening peripheral wall end portion. When the multi-well plate is manufactured by injection molding, the well marks may be formed together with the wells by placing inserts in the mold for manufacturing the multi-well plate. The well marks may be formed integral with the wells using a 3D printer. The wells having well marks, may be manufactured by shaping a member which has previously included the punch stamped well marks, into well shapes.

The multi-well plate according to this Embodiment described above is able to provide the same advantages and effects as those provided by the multi-well plate according to the First Embodiment, except for the advantages and effects based on the placements of the well marks S1.

Furthermore, in the multi-well plate according to this Embodiment, each well mark S3 is punch stamped to the inner peripheral surface 7b of the opening peripheral wall end portion 7. This punch stamped well mark S3 is made of the material constituting the multi-well plate. This results in less foreign matter production due to the provision of the well marks S3. Thus, the multi-well plate according to this Embodiment is able to prevent foreign matter, such as a material from the well marks S3, from being mixed into the samples in the wells 3, and improve the accuracy of experiment or test using the multi-well plate.

Fourth Embodiment

Next, a multi-well plate according to a Fourth Embodiment of the present invention will be described. The outline of the multi-well plate, the details of the wells, the details of the edge marks, and the symbols in the well marks in the multi-well plate according to this Embodiment are the same as those in the multi-well plate according to the First Embodiment. However, the placements of the well marks in the multi-well plate according to this Embodiment are different from that in the multi-well plate according to the Fourth First Embodiment. Below, the placements of the well marks in the multi-well plate according to this Embodiment will be described.

Placements of Well Marks

Figure 8:
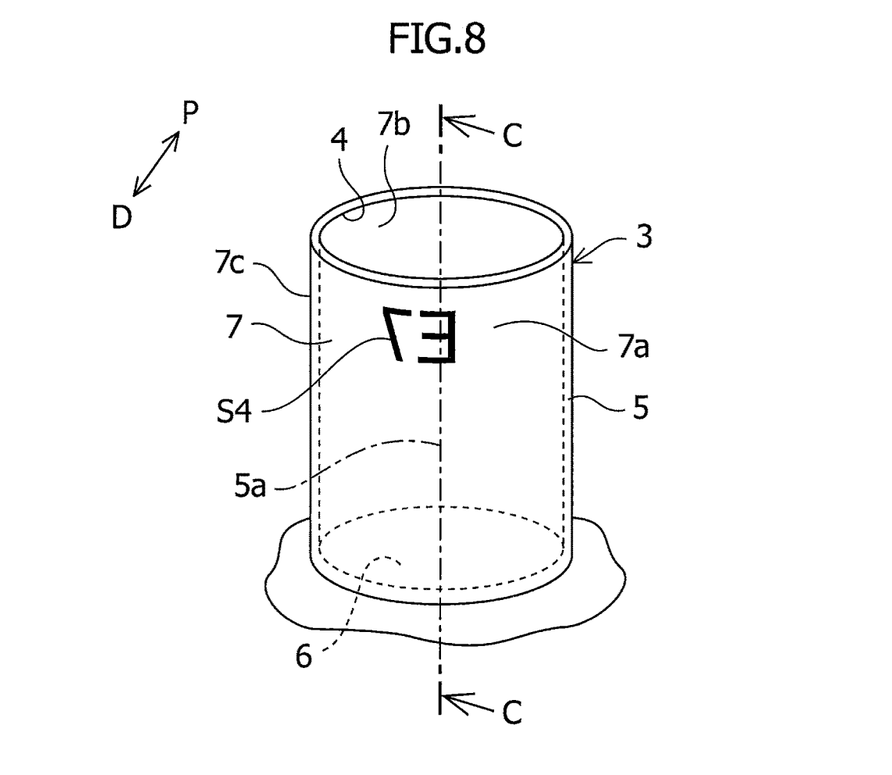
FIG. 8 is an enlarged perspective view schematically showing a well in a multi-well plate according to a Fourth Embodiment of the present invention, as viewed from an operator-distal side.
Figure 9:
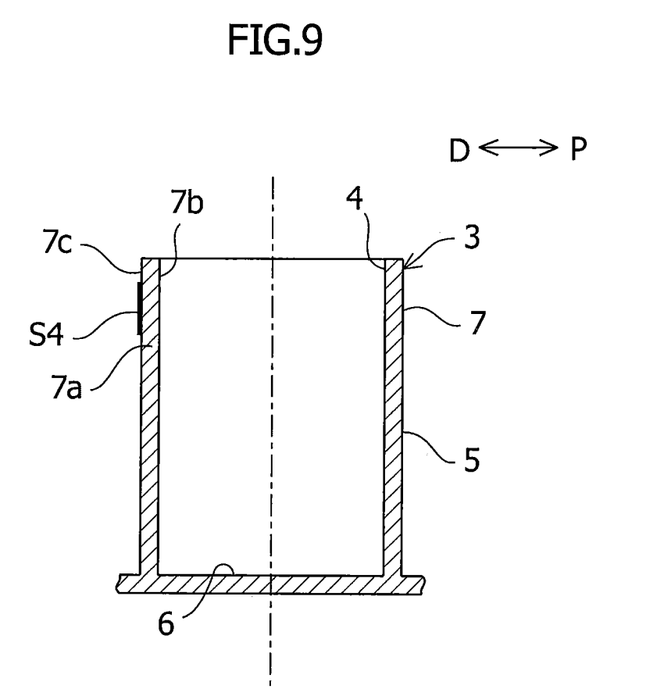
FIG. 9 is a cross-sectional view taken along line C-C of FIG. 8.

With reference to FIGS. 8 and 9, the placements of well marks S4 will be described. In the multi-well plate, each well mark S4 is placed adjacent to an outer peripheral surface 7c of the opening peripheral wall end portion 7 of the corresponding well 3. Furthermore, to allow an operator to view the well mark S4 which is placed adjacent to the outer peripheral surface 7c, through the inner peripheral surface 7b of the opening peripheral wall end portion 7, a region for placement of the well mark S4 in the opening peripheral wall end portion 7 is substantially transparent.

The region for placement of the well mark S4 may preferably extend from the position of the well mark S4 to the inner periphery of the peripheral wall 5, and may cover at least a circumferential area occupied by of the well mark S4, the circumferential area extending in the circumferential direction of the peripheral wall 5. Specifically, in FIGS. 8 and 9, the well mark S4 is provided onto the outer peripheral surface 7c of the opening peripheral wall end portion 7 with a colorant. Furthermore, preferably, the entire opening peripheral wall end portion 7, more preferably, the entire well 3, may be substantially transparent.

However, the present invention is not limited to the above, and the placements of the well marks may alternatively be the following. In the multi-well plate, each well mark may be provided onto the opening peripheral wall end portion by preparing a separate member with the well mark and placing the separate member directly on or adjacently to the outer peripheral surface of the opening peripheral wall end portion. Each well mark may be provided to the outer peripheral surface of the opening peripheral wall end portion by color change or removal in at least a portion of the outer peripheral surface of the opening peripheral wall end portion with laser marking. The well mark may be punch stamped to the outer peripheral surface of the opening peripheral wall end portion. The wells having well marks, may be manufactured by shaping a member which has been previously provided with the well marks, into well shapes. The well marks may be formed integral with the wells using a 3D printer.

The multi-well plate according to this Embodiment described above is able to provide the same advantages and effects as those provided by the multi-well plate according to the First Embodiment, except for the advantages and effects based on the placements of the well marks S1.

Furthermore, in the multi-well plate according to this Embodiment, each well mark S4 is placed adjacent to the outer peripheral surface 7c of the opening peripheral wall end portion 7, and the region for placement of the well mark S4 in the opening peripheral wall end portion 7 is substantially transparent. Thus, the sample that is input in each well 3, is separated from its well mark S4 by the substantially transparent region of the opening peripheral wall end portion 7. This prevents contact between the well marks S4 and the samples that are input in the wells 3, without compromising the ease of viewing the well marks S4 offered to the operator. Furthermore, even when, for example, the well marks S4 are provided using a colorant, the placement according to this Embodiment is able to prevent any peeled off colorant from the well marks S4 from being mixed into the samples in the wells 3. Thus, the multi-well plate according to this Embodiment is able to prevent foreign matter, such as a material from the well marks S4, from being mixed into the samples in the wells 3, and improve the accuracy of experiment or test using the multi-well plate.

Hereinabove, the Embodiments of the present invention have been described. It should be noted that the present invention is not limited to the above Embodiments, and various modifications and alterations may be made based on the technical concept of the present invention.

EXAMPLE

Example 1

Next, Example 1 will be described. In Example 1, test-purpose work was carried out using two multi-well plates of which each has the same configuration as in the First Embodiment of the present invention, and the workability in the work was checked. Specifically, these multi-well plates were manufactured using a transparent plastic material, and in the multi-well plates, each multi-well plate includes 96 wells arranged in a matrix with eight rows and twelve columns, and each of the 96 wells is provided with a well mark that has one of the symbols "A" to "H" that identifies the row containing the well, and one of the symbols "1" to "12" that identifies the column containing the well.

Each well mark was placed on a distal region, located closer to operator-distal than the central axis of the peripheral wall, of the opening peripheral wall end portion. Each symbol of the well marks had a height of 2.5 mm, a width of 1.5 mm, and black color. The font of the symbol was Gothic Helvetica. In the multi-well plates used in Example 1, the well marks were provided, using a colorant, onto an affixing surface of a sheet member, and the sheet member was affixed onto the inner peripheral surface of the opening peripheral wall end portion such that the affixing surface is in contact with the inner peripheral surface of the opening peripheral wall end portion.

As a test-purpose sample, water was previously placed in all the wells in one of these two multi-well plates (referred to as "first multi-well plate" below). As the test-purpose work of Example 1, a micropipette was used so as to move water contained in all the wells in the first multi-well plate, to all the wells in the other of the two multi-well plates (referred to as "second multi-well plate" below). Here, each source well in the first multi-well plate that initially contained water, and a target well in the second multi-well plate to which water was moved from this source well, were located in the same row and column as each other in their respective multi-well plates. Furthermore, in Example 1, the work time for completing the test-purpose work, and the number of operational errors of moving water to an incorrect well were measured. After three iterations of the test-purpose work, the average work time and the average number of operational errors in the work were calculated based on these three iterations.

Comparative Example 1

Next, Comparative Example 1 will be described. In Comparative Example 1, test-purpose work was carried out using two multi-well plates that were the same as those used in Example 1 except for absent of well mark, and the workability in the work was checked. In Comparative Example 1 as well, after three iterations of the same test-purpose work as in Example 1, the average work time and the average number of operational errors in the work were calculated based on these three iterations.

Table 1 below shows the values of the average work time and operational errors obtained in Example 1 and Comparative Example 1.

TABLE 1

| | Average Work Time [sec.] | Average Operational Errors |
|---|---|---|
| Example 1 | 283 | 0 |
| Comparative Example 1 | 341 | 0.67 |

As shown in Table 1, the average work time in Comparative Example 1 was 341 seconds; on the other hand, the average work time in Example 1 was 283 seconds. Thus, the work time in Example 1 was 17% less than the work time in Comparative Example 1. According to such a comparison of Example 1 with Comparative Example 1, it was confirmed that the present invention is able to improve working efficiency. Furthermore, as shown in Table 1, the average number of operational errors in Comparative Example 1 was 0.67; on the other hand, the average number of operational errors in Example 1 was 0. According to such a comparison of Example 1 with Comparative Example 1, it was confirmed that the present invention is also able to improve working accuracy.

REFERENCE SYMBOL LIST

1 Top portion
2 Bottom

3 Well
4 Opening
5 Peripheral wall
5a Central axis
7 Opening peripheral wall end portion
7a Distal region (One region)
7b Inner peripheral surface
7c Outer peripheral surface
8 Coating element
R Edge marks
r1 Row identification edge mark
r2 Column identification edge mark
S1, S2, S3, S4 Well mark
L1, L2 Straight line
P, D Arrow

The invention claimed is:

1. A multi-well plate comprising:
a top portion placed in a horizontal direction;
a bottom portion opposing the top portion in a direction crossing the horizontal direction; and
a plurality of wells of which each is formed so as to be recessed from the top portion toward the bottom portion, wherein
the plurality of wells are horizontally arranged in a matrix with a plurality of rows and a plurality of columns,
each of the wells has an opening formed at the top portion, and a peripheral wall extending from a periphery of the opening to the bottom portion,
at least two of the plurality of wells respectively include marks of which each contains at least one symbol, and
each of the marks is placed on a corresponding one of the peripheral walls adjacent an opening and on an inner surface of the corresponding one of the peripheral walls.

2. The multi-well plate according to claim 1, wherein, when at least one symbol is defined for each of the rows so as to identify the plurality of rows separately from one another, and at least one symbol is defined for each of the columns so as to identify the plurality of columns separately from one another, each of the marks respectively provided to the at least two wells, contains the at least one symbol identifying one of the rows at which the corresponding one of the wells is arranged, and the at least one symbol identifying one of the columns at which the corresponding one of the wells is arranged.

3. The multi-well plate according to claim 1, wherein each of the marks is placed on one region of the inner surface of the corresponding one of the peripheral walls, the one region being closer to one-way of a directional element of the horizontal direction than a central axis of the peripheral wall.

4. The multi-well plate according to claim 1, wherein each of the marks is formed using a colorant and is placed along the inner surface of the corresponding one of the peripheral walls.

5. The multi-well plate according to claim 4, wherein the marks are covered with a transparent coating element.

6. The multi-well plate according to claim 1, wherein each of the marks is provided to the inner surface of the corresponding one of the peripheral walls by color change or removal with laser marking.

7. The multi-well plate according to claim 1, wherein each of the marks is punch stamped to the inner surface of the corresponding one of the peripheral walls.

* * * * *

UNITED STATES PATENT AND TRADEMARK OFFICE
CERTIFICATE OF CORRECTION

PATENT NO. : 10,967,377 B2
APPLICATION NO. : 16/314819
DATED : April 6, 2021
INVENTOR(S) : Yoshio Kato It is certified that error appears in the above-identified patent and that said Letters Patent is hereby corrected as shown below:

In the Specification

Column 13, Line 55: Please correct "Third First Embodiment" to read -- First Embodiment --

Column 14, Line 41: Please correct "Fourth First Embodiment" to read -- First Embodiment --

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*